US007371928B2

(12) United States Patent
Suh et al.

(10) Patent No.: US 7,371,928 B2
(45) Date of Patent: May 13, 2008

(54) PLANT SEED-SPECIFIC EXPRESSION PROMOTER DERIVED FROM SESAME AND SEED-SPECIFIC EXPRESSION VECTOR COMPRISING THE PROMOTER

(75) Inventors: Mi-Chung Suh, Seoul (KR); Mi-Jung Kim, Seoul (KR); Hee-Ja Kim, Seoul (KR); Chung-Han Chung, Busan (KR); Jae-Ho Pyee, Gunpo (KR); Nam-In Hyung, Cheonan (KR)

(73) Assignee: Korea Chungang Educational Foundation, Seoul (KR)

( * ) Notice: Subject to any disclaimer, the term of this patent is extended or adjusted under 35 U.S.C. 154(b) by 232 days.

(21) Appl. No.: 10/534,128

(22) PCT Filed: Nov. 11, 2003

(86) PCT No.: PCT/KR03/02415

§ 371 (c)(1),
(2), (4) Date: May 6, 2005

(87) PCT Pub. No.: WO2004/044205

PCT Pub. Date: May 27, 2004

(65) Prior Publication Data
US 2007/0101458 A1 May 3, 2007

(30) Foreign Application Priority Data
Nov. 11, 2002 (KR) .................. 10-2002-0069589
Apr. 18, 2003 (KR) .................. 10-2003-0024776

(51) Int. Cl.
*C12P 7/62* (2006.01)
*C12P 11/00* (2006.01)
*C07H 21/04* (2006.01)
*A01H 1/00* (2006.01)

(52) U.S. Cl. ............... 800/295; 435/6; 435/69.1; 435/320.1; 435/410; 435/419; 435/468; 536/23.1; 536/24.1; 800/278; 800/281; 800/284; 800/287

(58) Field of Classification Search .............. None
See application file for complete search history.

(56) References Cited

U.S. PATENT DOCUMENTS 5,530,186 A * 6/1996 Hitz et al. .................. 800/264

(Continued)

FOREIGN PATENT DOCUMENTS

KR 20010099065 11/2001

OTHER PUBLICATIONS

Oommenn et al (1994) The Plant Cell 6:1789-1803).*
Hauschild, et al (1998) Isolation and analysis of the gene bbe1 encoding the berberine bridge enzyme from the California poppy *Eschscholzia californica* Plant Molec. Biol. 36:473-478.*
Facchini et al, (1998) Plant Physiol. 118:69-81.*

*Primary Examiner*—Anne Marie Grunberg
*Assistant Examiner*—Brendan O. Baggot
(74) *Attorney, Agent, or Firm*—Ked & Associates, LLP

(57) ABSTRACT

Provided are a seed-specific expression promoter derived from sesame microsomal oleic acid desaturase (Si-FAD2) gene, an intron for expression enhancement, a seed-specific expression vector including the promoter and/or the intron, and a transgenic plant transformed with the seed-specific expression vector. Therefore, a useful product can be produced in a seed-specific manner or a common product in a seed can be functionally modified. Also, the promoter can be used together with the intron for expression enhancement, thereby increasing the expression level of an inserted gene in a seed. Therefore, it is very useful in development of a transgenic plant which induces large-scale expression of a foreign gene in a seed-specific manner.

10 Claims, 12 Drawing Sheets

U.S. PATENT DOCUMENTS

| | | | |
|---|---|---|---|
| 2002/0045229 A1 | 4/2002 | Qin et al. | 435/183 |
| 2002/0059656 A1 | 5/2002 | Wang et al. | 800/278 |
| 2002/0061567 A1 | 5/2002 | Tang et al. | 435/183 |
| 2002/0069426 A1 | 6/2002 | Boronat et al. | 800/278 |
| 2002/0081691 A1 | 6/2002 | Hillman et al. | 435/191 |
| 2002/0166144 A1 | 11/2002 | Green et al. | 800/281 |

* cited by examiner

```
ATGGGAGCCGGAGGACGCATGTCTGATCCAACAACGAAAGACGAACAAAAGAAGAACGCG
 M  G  A  G  G  R  M  S  D  P  T  T  K  D  E  Q  K  K  N  P
CTCCAACGGGTGCCTTACGCAAAGCCTCCATTCACACTCGGTGACATCAAGAAGGCCATT
 L  Q  R  V  P  Y  A  K  P  P  F  T  L  G  D  I  K  K  A  I
CCACCACACTGCTTCGAGAGATCCGTCAGCCGTTCGTTCTCCTATGTCGTTTACGATCTC
 P  P  H  C  F  E  R  S  V  S  R  S  F  S  Y  V  V  Y  D  L
GTCATTGTTTCCTTCTCTACTACAATTGCGAGTTCTTACTTCCATCTGCTGCCATCCCCA
 V  I  V  F  L  L  Y  Y  I  A  T  S  Y  F  H  L  L  P  S  P
TACTGCTACCTAGCTTGGCCCATTTACTGGGCTGTACAAGGCTGCGTTTGCACGGAATC
 Y  C  Y  L  A  H  P  I  Y  H  A  V  Q  G  C  V  C  T  G  I
TGGGTCATTGCCCATGAATGTGGCCACCATGCATTCAGCGATTACCAGTGGCTTCACGAC
 W  V  I  A  H  E  C  G  H  H  A  F  S  D  Y  Q  W  L  D  D
ACAGTTGGCCTCATCCTGCACTCTGCCCTGCTCGTGCCGTATTTCTCATGGAAATACAGC
 T  V  G  L  I  L  H  S  A  L  L  V  P  Y  F  S  W  K  Y  S
CACCGCCGCCACCACTCCAACACTGGATCCCTTGAGCGTGACGAAGTCTTCGTCCCAAAG
 H  R  R  H  H  S  N  T  G  S  L  E  R  D  E  V  F  V  P  K
CCAAAATCCAGAGTCTCGTGGTACTCCAAATACTTGAACAATCCACTTGGCAGAGTCATC
 P  K  S  R  V  S  W  Y  S  K  Y  L  N  N  P  L  G  R  V  I
ACACTTGTGGTTACTCTTACTCTCGGTTGGCCTCTATACTTGCTGTTTAATGTCTCTGGC
 T  L  V  V  T  L  T  L  G  W  P  L  Y  L  L  F  N  V  S  G
AGGCCTTACAACCGTTTTGCATGCCACTTTGACCCATATGGTCCAATATATAATGACCGT
 R  P  Y  N  R  F  A  C  H  F  D  P  Y  G  P  I  Y  N  D  R
GAGAGACTTCAAATCTTCATCTCCGATGCTGGTATAATTGCTGCTGTATGTGTGTTTAT
 E  R  L  Q  I  F  I  S  D  A  G  I  I  A  A  V  C  V  L  Y
CGTGTTGCTTTGGTCAAAGGGTTGGCTTGGCTGGTATGTGTTTATGGGGTACCGTTACTC
 R  V  A  L  V  K  G  L  A  W  L  V  C  V  Y  G  V  P  L  L
ATTGTCAACGGTTTCCTTGTTTTGATCACATTCCTTCAGCACACTCACCCTTCGTTGCCG
 I  V  N  G  F  L  V  L  I  T  F  L  Q  H  T  H  P  S  L  P
CACTATGATTCTTCCGAGTGGGACTGGCTAAGGGGAGCTCTTGCAACTGTCGACAGAGAT
 H  Y  D  S  S  E  W  D  W  L  R  G  A  L  A  T  V  D  R  D
TATGGGGTGCTAAATAAGGTGTTCCATAACATCACAGATACGCACGTGACTCACCACTT
 Y  G  V  L  N  K  V  F  H  N  I  T  D  T  H  V  T  H  H  L
TTCTCAACGATGCCACATTACCATGCAAATGGAGGCAACTAAGGCAATCAAGCCGATACTG
 F  S  T  M  P  H  Y  H  A  N  E  A  T  K  A  I  K  P  I  L
GGCCAGTATTATCAGTTTGATGGAACCGCGTTTTACAAGGCGATGTGGAGGGAGGCAAAG
 G  Q  Y  Y  Q  F  D  G  T  P  F  Y  K  A  M  W  R  E  A  K
GAATGTCTGTATGTCGAGCCAGACGAGAGTACTCCAGACAAGGGTGTATTCTGGTACAAG
 E  C  L  Y  V  E  P  D  E  S  T  P  D  K  G  V  F  W  Y  K
```

FIG. 1c

AACAAGTTCTGAAGCCGAATAACATGTGGTTAGTGAAAATGGCGTGTTCTTATTTTGTCC
N K F -
TATGGAGATGGAGGAACATCATCATGTTTTGTTTTTGTTCTTATAAGATGCGTCCTTTGT
TAGTGTATTCTCTGCATGTAATAAAATAAACTTCTACCCGAAACCTTGTCTGTGCTGGTC
GGATTCTAGTTCTGCAATAAATTGTCAAGTTTAGTG

FIG. 2a

FIG. 2b

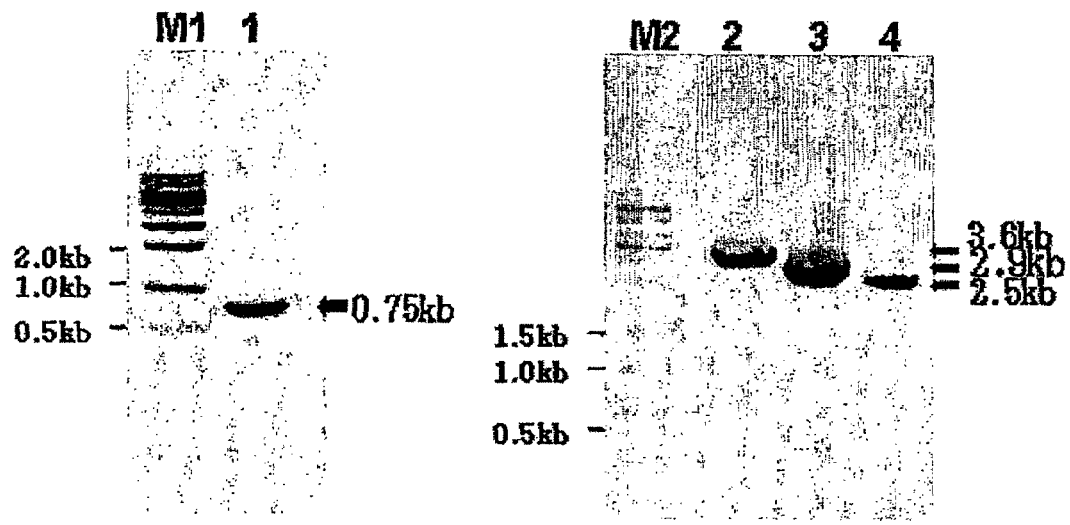

FIG. 3

CATATGTGAAATGTAATGGAAAATGCGACAAGAATTGCAATAGAGAAAATCCAATTTGCAGAGATTA
CATGAAAAGAATTTGTACAAATAGCATATATATGTTAAAATGAAATGGACATGCCACATTATGTGG
AATAAAAAAGACAATTTGCTTGGAATTAATTATAGAATAAATGTGTTACATTTAATATGTGATTAAT
CACTTTTTTTGAATTGTACATCTATCACATGACAAGTTCATTATATTTGACATATAATTTGTTTATG
TCTAGTCAAGCCTAATTAAATTTCTCGGAAAGCACAAAATTTTTTTGTCCTAACCAGGTTTGAACAA
CCAAACAAATCACAAAGCAGGTGTATCGCACTTGCGATGTGATCGGTCACTTTTTCTAAATTGTACA
TCATTCACACGACAACTGTATTGTGCTCCAAGTTCAATTGAGTGCGGTTGGAGCTATAATTTCCTTG
AACACACAATGTGGAATGTGCACACTCCATGTGGGCCAATGAGCGGATGACACGTGGCGGGCAACTT
ACCTCGTTACGTTGAGGCATGCATGAAAGGGGGATCTCTTGAGGTGGAGGGGTGGGGGCGGGGGTTG
GGGGGGGGCCCCTCCTCAGACAGGTCTATATTTATGAGACCTCGTAAGGCAGAACGC

```
-179  GGAATGTGCACACTCCATGTGGGCCAATGAGCGGATGACACGTGGCGGG
      CAACTTACCTCGTTACGTTGAGGCATGCATGAAAGGGGGATCTCTTGAGGTGGA
      GGGGTGGCGGCGGGGGTTGGGGGG  -53
```

PLANT SEED-SPECIFIC EXPRESSION PROMOTER DERIVED FROM SESAME AND SEED-SPECIFIC EXPRESSION VECTOR COMPRISING THE PROMOTER

TECHNICAL FIELD

The present invention relates to a plant seed-specific expression promoter derived from a genomic gene (Si-FAD2) encoding the microsomal oleic acid desaturase of sesame and an intron for expression enhancement. The present invention also relates to a plant seed-specific expression vector containing the promoter and/or the intron and a transgenic plant transformed with the seed-specific expression vector.

BACKGROUND ART

Fatty acids of plants are important components that make cell membranes and seed oils. In particular, microsomal oleic acid desaturase, which is present in the endoplasmic reticulum of plant cells, is an enzyme that catalyzes the conversion of monounsaturated fatty acid, oleic acid, at the sn-1 and sn-2 positions of phosphatidylcholine, into diunsaturated fatty acid, linoleic acid.

There have been reports about presence of genomic genes (FAD2) encoding the microsomal oleic acid desaturase in *Arabidopsis, Petunia,* and cotton. According to the reports, while one FAD2 gene is present on the genome of *Arabidopsis,* two or more FAD2 genes are present on each genome of *Petunia* and cotton [Okuley et al., 1994, Plant Cell; Verwoert et al., 2000, Biochemistry Society Transactions; Pirtie et al., 2001, Biochimica et Biophysica Acta]. In particular, it has been known that when two or more FAD2 genes are present on a plant genome, at least one is involved in production of linoleic acid that accumulates in a seed oil. Until now, while the presence of the FAD2 gene in the above-mentioned three plants has been reported, no studies on the functional analysis of its promoter have been reported.

Recently, many attempts have been made to improve genetic characteristics of plants using genetic engineering technology. In this respect, expression of a useful foreign gene in a transgenic plant requires a promoter for the gene expression. For this, conventionally, a promoter derived from a cauliflower mosaic virus (CaMV35S) gene that induces gene expression at all tissues of a plant has been widely used. However, this promoter cannot induce seed-specific gene expression. Meanwhile, there have been reports about promoters that induce tissue-specific expression, for example, seed-specific expression [Plant Cell Technology, 1991, 3: 568-576], leaf- or flower-specific expression [Science, 1990, 250: 931-936], and root-specific expression [Plant Cell Technology, 1991, 3: 577-587]. However, the above seed-specific expression promoter induces gene expression during whole stages for seed development, not during a specific development stage.

In view of these problems, based on the fact that the microsomal oleic acid desaturase derived from sesame is specifically expressed during a seed development stage, the present inventors cloned the genomic gene encoding microsomal oleic acid desaturase and its promoter, inserted the promoter into a binary vector and a transient expression vector, and then introduced the vectors into the seeds of model plants, *Arabidopsis* and sesame. As a result, the present inventors found that the sesame microsomal oleic acid desaturase (Si-FAD2) promoter is a novel promoter that induces the expression of a foreign gene in a seed development stage-specific manner, and completed the invention.

Furthermore, a 127 bp active fragment of the promoter essential for the seed-specific expression has been identified. Also, the present inventors found that when the promoter is used together with an intron present on the Si-FAD2 gene, the expression level of a foreign gene in a seed is enhanced by at least 40-fold, and completed the invention. In this regard, the intron is useful in high expression of a useful foreign gene.

Therefore, the present invention provides a seed-specific, in particular, a seed development stage-specific expression promoter derived from the Si-FAD2 gene and a 127 bp active fragment thereof.

The present invention also provides an intron that enhances the expression level of a foreign gene under the control of the above-described seed-specific expression promoter.

The present invention also provides a seed-specific expression vector containing the above-described promoter and/or intron and a transgenic plant transformed with the seed-specific expression vector.

The present invention also provides a method for expressing a foreign gene in a transgenic plant using the above promoter. This method is useful in producing a useful product in a seed development stage-specific manner or functionally modifying conventional product in seeds.

DISCLOSURE OF THE INVENTION

Therefore, according to an aspect of the present invention, there is provided a seed-specific expression promoter comprising an active fragment of nucleotides −179 to −53 of SEQ ID NO: 3. Preferably, the present invention provides a seed-specific expression promoter comprising the nucleotide sequence as set forth in SEQ ID NO: 3.

The nucleotide sequence of SEQ ID NO: 3 comprises nucleotides that extend from position −660 to −1 from a transcription initiation site of the sesame microsomal oleic acid desaturase (Si-FAD2) gene which is expressed in a seed-specific manner. In this regard, it is expected that the nucleotide sequence contains a seed-specific transcription regulatory site as well as a TATA box and a CAAT-box which are common promoter sequences for recognition of the transcription initiation site of a plant gene. Also, nucleotides that extend from position −179 to −53 of SEQ ID NO: 3 correspond to the promoter active fragment (127 bp) essential for seed-specific expression. That is, when these nucleotides are deleted, promoter activity is greatly decreased.

According to another aspect of the present invention, there is provided an intron for enhancement of gene expression, comprising nucleotides 149 to 1722 of SEQ ID NO: 1.

The nucleotides 149 to 1722 of SEQ ID NO: 1 corresponds to the intron present in 5'-untranslated region of the Si-FAD2 gene. When the promoter is used together with the intron, the expression level of a foreign gene in a seed can be increased by at least 40-fold.

According to another aspect of the present invention, there is provided a seed-specific expression vector comprising the above-described promoter and/or intron.

Preferably, the seed-specific expression vector is constructed by inserting the promoter upstream of a foreign gene of a binary vector. The binary vector that can be used herein may be one that contains the left and right borders (BR and BL) of T-DNA capable of transforming a plant in the presence of the Ti-plasmid of *Agrobacterium tumefa-*

*ciens*. For example, pGA series, pCG series, pCIT series, pGPTV series, pBECK2000 series, or pGreen series vectors may be used. It is preferable to use pBI series vectors (Clontech, America), easily commercially available in the pertinent art. The foreign gene that can be used herein may be a target gene or a reporter gene derived from an external source that is to be expressed in a plant of interest.

In the seed-specific expression vector of the present invention, the promoter is operably linked to a foreign gene contained in the binary vector. By "operably linked" is intended a functional linkage between a promoter and a second sequence, wherein the promoter sequence initiates and mediates transcription of the DNA sequence corresponding to the second sequence. For example, there is a pBinSiFAD2-GUS expression vector (FIG. 4B) constructed by inserting the promoter into a pBI101 binary vector containing β-glucuronidase (GUS) gene which is a reporter gene. It is understood that the GUS reporter gene can be replaced with a desired foreign gene.

Furthermore, in the seed-specific expression vector of the present invention, the promoter and the intron are operably linked to a foreign gene contained in the binary vector. For example, there is a pSiW6-P2.4 expression vector (FIG. 9A) constructed by inserting the promoter and the intron into the pBI101 binary vector containing the GUS reporter gene. It is understood that the GUS reporter gene can be replaced with a desired foreign gene.

Preferably, the seed-specific expression vector of the present invention is constructed by inserting the promoter upstream of a foreign gene of a transient expression vector. Any transient expression vector can be used provided that it allows a foreign gene to be transiently expressed in plant tissues. For example, pBI221 [Mitsuhara et al., 1996], pMG221 [Maas et al., 1991], pUbiGUS [Christensen and Quail, 1996], or ACT1-D [McElroy et al., 1990] may be used. It is preferable to use pBI221 (Clontech, America) easily commercially available in the pertinent art. The foreign gene that can be used herein may be a target gene or a reporter gene derived from an external source that is to be expressed in a plant of interest.

In the seed-specific expression vector of the present invention, the promoter is operably linked to a foreign gene contained in the transient expression vector. For example, there is a pSiFAD2-GUS expression vector (FIG. 8A) constructed by inserting the promoter into a pBI221 transient expression vector containing the GUS reporter gene. It is understood that the GUS reporter gene can be replaced with a desired foreign gene.

According to another aspect of the present invention, there is provided a transgenic plant cell or plant transformed with the seed-specific expression vector.

When the seed-specific expression vector is a binary vector, a plant is transformed by floral dip method [Clough and Bent, 1998, The Plant Journal]. When the seed-specific expression vector is a transient expression vector, a plant is transformed by particle bombardment method [Lacorte et al., 1997, Plant Cell Reports]. The seed-specific expression vector can be used for transformation of all plants including dicot plant, monocot plant, sexual reproductive plant, and asexual reproductive plant. *Arabidopsis* and sesame (*Sesamum indicum*) are used herein.

According to yet another aspect of the present invention, there is provided a method for expressing a foreign gene in a transgenic plant transformed with the seed-specific expression vector.

The foreign gene may be any one that is wanted to be expressed in a plant. The foreign gene is positioned downstream of the promoter and/or the intron in the seed-specific expression vector. When needed, the expression of the foreign gene can be coupled with the expression of a reporter gene.

The present invention provides a seed-specific expression promoter of the Si-FAD2 gene and a method for expressing a foreign gene in a transgenic plant using the promoter. Therefore, the present invention is useful in producing a useful product in a seed development stage-specific manner or functionally modifying a common product in a seed. Also, according to the present invention, the promoter can be used together with an intron for expression enhancement, thereby increasing the expression level of a foreign gene in a seed by at least 40-fold. Therefore, the present invention can be used in development of a transgenic plant which induces high expression of a foreign gene in a seed-specific manner.

BRIEF DESCRIPTION OF THE DRAWINGS

FIG. 1 is the nucleotide sequence (SEQ ID NO: 1) of the gene encoding sesame microsomal oleic acid desaturase (Si-FAD2) and the amino acid sequence (SEQ ID NO: 2) deduced therefrom;

FIG. 2 is a diagram of Si-FAD2 gene;

FIG. 3 is the nucleotide sequence (SEQ ID NO: 3) of the promoter of Si-FAD2 gene;

BEST MODE FOR CARRYING OUT THE INVENTION

Figure 4A:
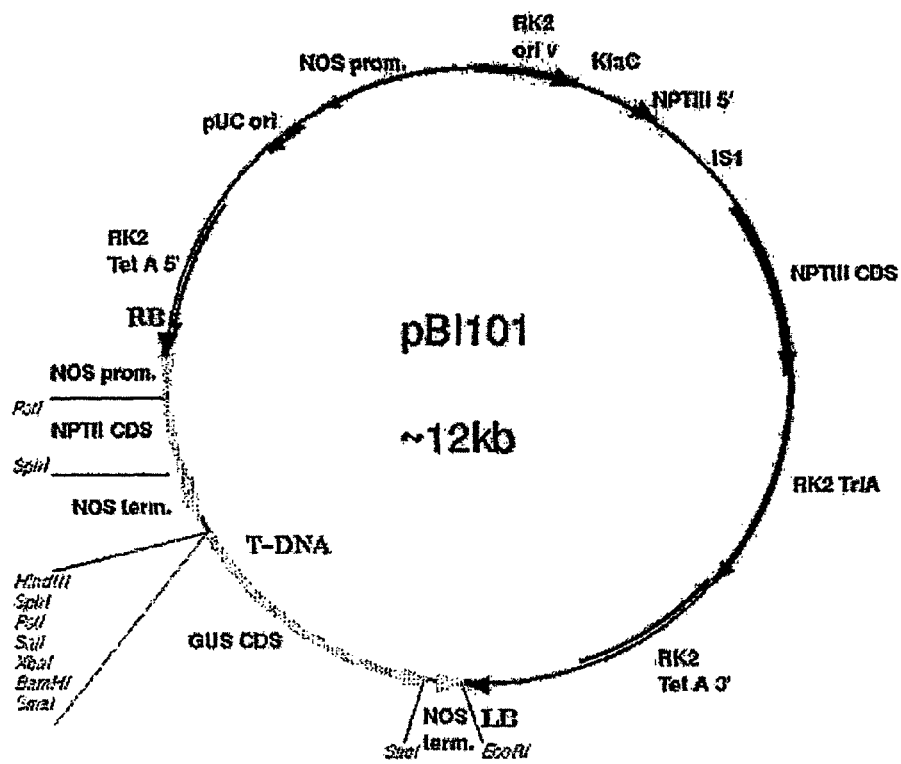
FIG. 4A is a genetic map of a pBI101 binary vector containing β-glucuronidase (GUS) gene used in a preferred embodiment of the present invention.

Hereinafter, the present invention will be described more specifically by Examples. However, the following Examples are provided only for illustrations and thus the present invention is not limited to or by them.

EXAMPLE 1

Cloning and Sequencing of Genomic Gene Encoding Sesame Microsomal Oleic Acid Desaturase (Si-FAD2)

Figure 1A:
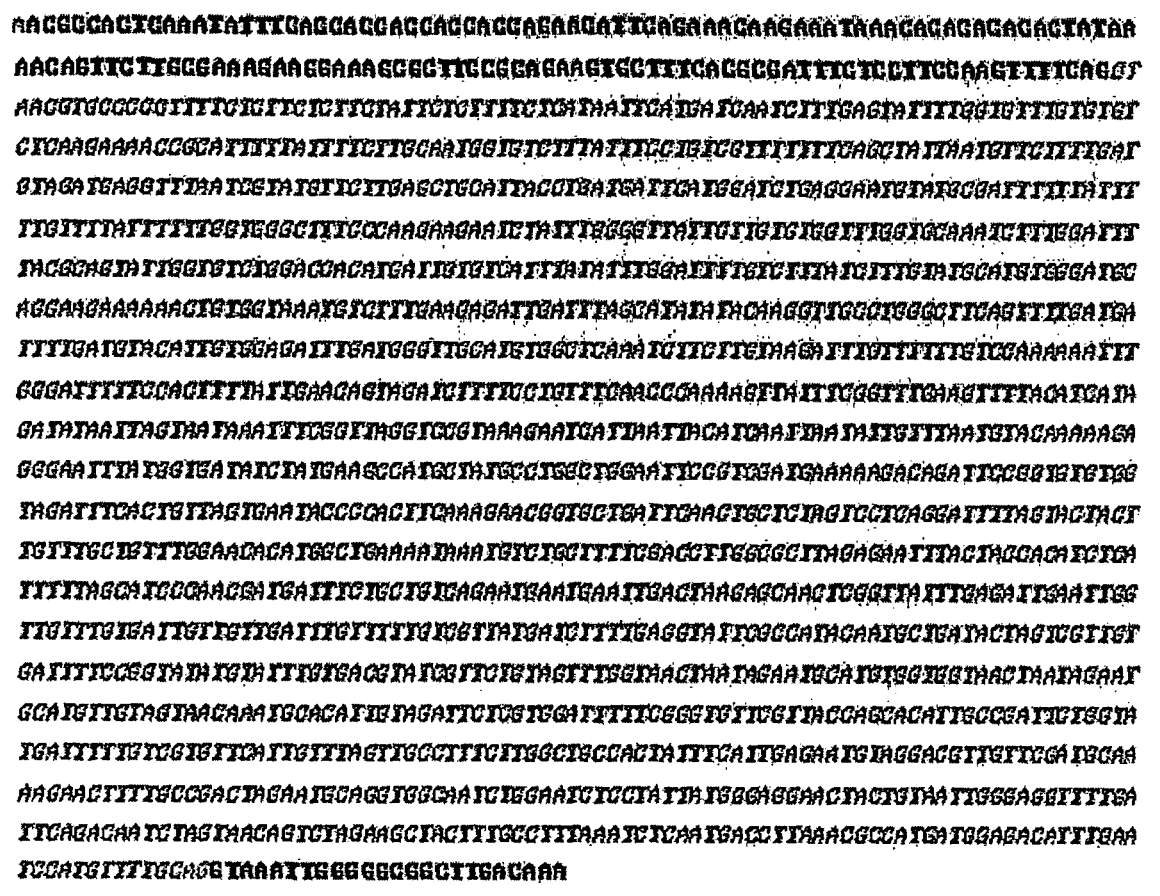

In order to obtain genomic clones of seed-specific Si-FAD2 gene, genomic DNA was extracted from young leaves of *Sesamum indium* [Dellaporta et al., 1984, in Molecular Biology of Plants]. The genomic clones of the Si-FAD2 gene were isolated by polymerase chain reaction (PCR) using a pair of primers (forward primer W6-1: 5'-GACAAAATGG-GAGCCGGAGGACGCATGT-3' and reverse primer W6-R1: 5'-CGGCTTCAGAACTTGTTCTTGTACCAGA-3') designed from cDNA (GenBank Accession No: AF192486) disclosed by Jin et al. [2001, Plant Science]. The genomic clones thus isolated were cloned into a pGEM-T vector (Promega, America) followed by sequencing using ABI Bigdye cycle sequencing kit (PE Applied Biosystems, America). In comparison between the genomic clones and the cDNA, it was demonstrated that the genomic clones and the cDNA were identical except 9 bases (CGGCACGAG) from the 5'-end of the cDNA. The genomic clones of the Si-FAD2 gene contained a single bulky intron containing 1,574 bp in the 5'-untranslated region (UTR). However, there was no intron in the coding region. The nucleotide sequence (SEQ ID NO: 1) of the Si-FAD2 gene and the amino acid (SEQ ID NO: 2) deduced therefrom are shown in FIG. 1. The first base "A" is a translation initiation base, and bases in italic type (GT-AG) are those of the intron contained in the 5'-UTR.

EXAMPLE 2

Sequencing of 5'-Upstream Region of Si-FAD2 Gene

In order to clone the promoter of the Si-FAD2 gene, inverse PCR was performed using the genomic DNA of the Si-FAD2 gene digested with NdeI restriction site. Generally, inverse PCR has been frequently used in detection of unknown regions such as a promoter [Digeon et al., 1999, Plant Molecular Biology]. For inverse PCR, the genomic DNA was digested with NdeI restriction enzyme and self-ligated by T4 DNA ligase (BM, Germany) to prepare a template DNA. Inverse PCR was performed in two steps to obtain specific PCR products. First, the first PCR was performed using gene-specific primers (W6-1: 5'-GA-CAAAATGGGAGCCGGAGGACGCATGT-3' and W6-R6: 5'-GGGGGCACGTTACCTGAAAACTTGGAAG-3') to obtain a first PCR product. Then, the second PCR was performed using the first PCR product as a template with inner primers (W6-2: 5'-GGCTTTGGGACGAAGACT-TCGTCACGCT-3' and W6-R7: 5'-CGCGTGAAAGCACT-TCTGCGGAAGCGC-3'). As a result, the 5'-upstream region (about 750 bp, −660 to +90) of the Si-FAD2 gene was obtained. FIG. 2A shows a diagram of the Si-FAD2 gene. Here, SiW6F1, SiW6R1, W6R3, W6R5, and W6R1 indicate the positions of primers as used in FIG. 2B.

In order to determine whether the obtained fragment is the 5'-upstream region of the Si-FAD2 gene, PCR was performed using the gene-specific primers (SiW6F1, SiW6R1, W6R1, W6R3, and W6R5) designed from the 5'-end of the 750 bp fragment and the internal region of the Si-FAD2 gene. As a result, ft was demonstrated that the 750 bp fragment is the 5'-upstream region of the Si-FAD2 gene. FIG. 2B shows a PCR result of the genomic DNA of sesame leaf FAD2 gene using the primers of FIG. 2A. Here, M1 and M2 represent DNA size markers. Lane 1 is a PCR product obtained using the SiW6F1 (5'-CCGAAGCTTCATATGT-GAAATGTAATGGAAAATGCGAC-3') and the SiW6R1 (5'-CTTGGATCCTTGGAAGGAGAAATCGCGT-GAAAGCAC-3'). Lane 2 is a PCR product obtained using the SiW6F1 and the W6R1 (5'-CGGCTTCAGMCTTGT-TCTTGTACCAGA-3'). Lane 3 is a PCR product obtained using the SiW6F1 and the W6R5 (5'-GGAGAACGAACG-GCTGACGGATCTCTCG-3'). Lane 4 is a PCR product obtained using the SiW6F1 and the W6R3 (5'-GGCTTTGG-GACGGAAGACTTCGTCACGCT-3'). The 5'-upstream region of the Si-FAD2 gene was sequenced. The nucleotide sequence (SEQ ID NO: 3) of the promoter region of 1 to 660 bp long upstream from a transcription initiation site is shown in FIG. 3.

EXAMPLE 3

Identification of Transcription Initiation Site of Si-FAD2 Gene

In order to determine the activity of the seed-specific promoter of the Si-FAD2 gene, the transcription initiation site of the gene must be identified. For this, cRACE (circular first-strand cDNA-mediated rapid amplification of cDNA ends) was performed according to Maruyama et al method [Nucleic Acid Research, 1995]. First, total RNA was isolated from sesame seeds. Then, cDNA was synthesized with a gene-specific primer (5'-GGTAGCAGTATGGGGATG-GCAGCAGATGGAAGTA) which was phosphorylated by T4 polynucleotide kinase (Takara) and reverse transcriptase (BM), and the 5'- and 3'-ends of the cDNA were ligated with T4 RNA ligase (NEB). PCR was performed using the resultant cDNA as a template with gene-specific primers (W6-5: 5'-GAAGAACCCCCTCCAACGGGTGCC-3' and W6-R9: 5'-CCGATCACATCGCAAGTGCGATACAC-CTG-3'). As a result, it was demonstrated that the first base "A" of FIG. 1 is a transcription initiation base.

EXAMPLE 4

Analysis of Si-FAD2 Promoter Activity in Arabidopsis

Figure 4B:
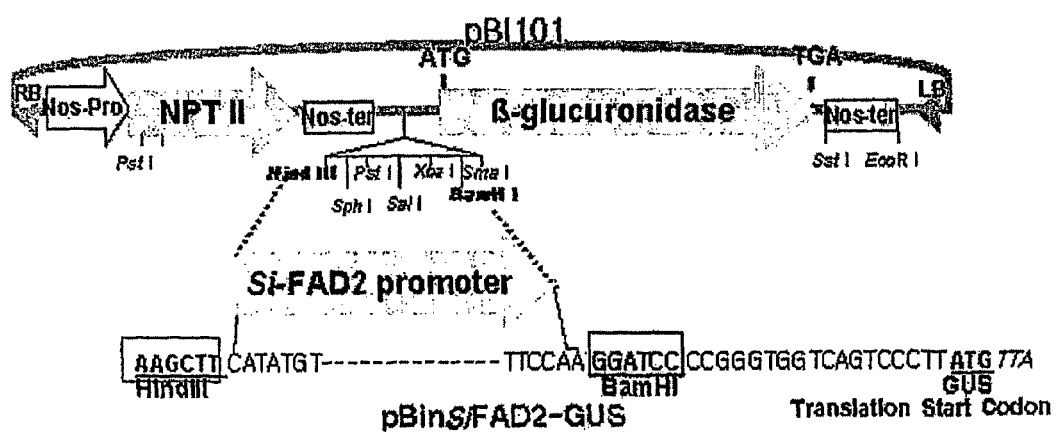
FIG. 4B is a diagram of a pBinSiFAD2-GUS expression vector constructed by inserting Si-FAD2 promoter into pBI101 binary vector containing GUS gene.

In order to analyze the Si-FAD2 promoter activity in Arabidopsis, a pBinSiFAD2-GUS expression vector containing the cloned Si-FAD2 promoter and GUS reporter gene was constructed. First, PCR was performed using sesame genomic DNA as a template with a pair of primers, the SiW6F1 (5'-CCGAAGCTTCATATGTGAAATG-TAATGGAAAATGCGAC-3') and the SiW6R1 (5'-CTTG-GATCCTTGGAAGGAGAAATCGCGTGAAAGCAC-3'). As a result, the promoter region (−660 to +141) of the Si-FAD2 gene was obtained. The promoter region and a pBI101 binary vector (Cat. # 6017-1, Clontech, America) of which genetic map is shown in FIG. 4A were digested with the same restriction enzymes HindIII and BamHI. The digested promoter region and pBI101 binary vector were ligated using T4 DNA ligase to construct the pBinSiFAD2-GUS expression vector. FIG. 4B shows a diagram of the pBinSiFAD2-GUS expression vector in which the promoter region was cloned into the HindIII-BamHI restriction sites of the pBI101 binary vector. Here, GUS is a reporter gene encoding β-glucuronidase (which can be replaced with a foreign gene to be expressed). NPTII is a kanamycin resistance marker gene encoding neomycin phosphotransferase II. Nos-pro and Nos-ter are respectively the promoter and terminator for plant expression of the NPTII.

Figure 4C:
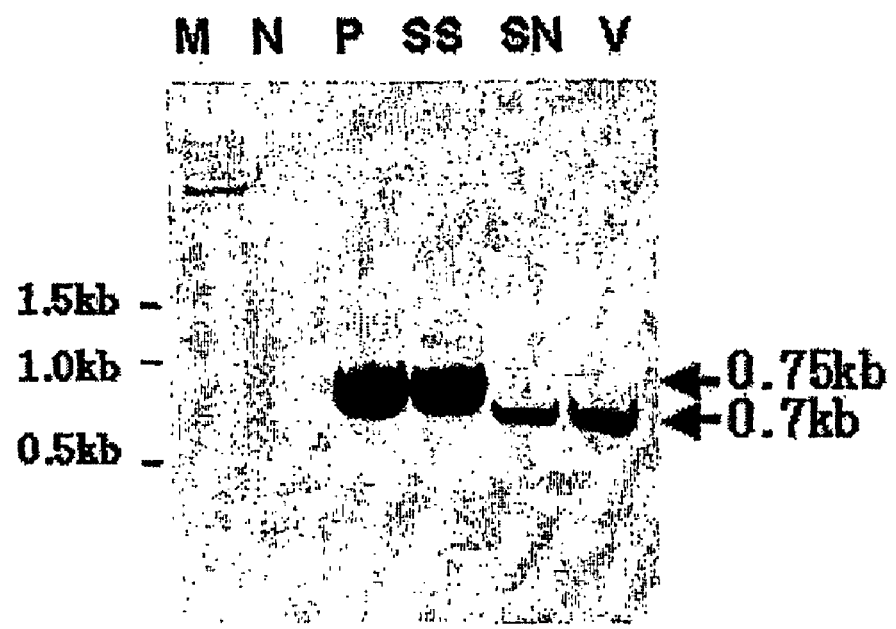
FIG. 4C is a polymerase chain reaction (PCR) result with vector gene-specific primers in *Agrobacteria* transformed with a pBinSiFAD2-GUS expression vector containing Si-FAD2 promoter or a pBI121 binary vector containing CaMV35S promoter.

The pBinSiFAD2-GUS expression vector thus constructed was introduced into Agrobacterium tumefaciens C58C1 [Suh et al., 2002, Molecules and Cells] by freeze-thaw method [An, G. 1987, Methods in Enzymology]. According to the freeze-thaw method, the Agrobacteria were suspension-cultured in YEP media until O.D=0.5 followed by resuspending in 20 mM $CaCl_2$ solution. The suspension thus obtained was mixed with the pBinSiFAD2-GUS expression vector and incubated in liquid nitrogen for 1 minutes and then at 37° C. for 2 minutes. FIG. 4C shows a PCR result of the Agrobacteria transformed with the pBinSiFAD2-GUS expression vector of FIG. 4B and pBI121 binary vector (Cat. # 6018-1, Clontech, America) containing CaMV35S promoter using vector gene-specific primers. Here, M is a DNA size marker, N is a PCR product of pBI121 binary vector-containing Agrobacteria using the SiW6F1 and SiW6R1 (negative control), P is a PCR product of pBinSiFAD2-GUS expression vector-containing Escherichia. coli using the SiW6F1 and SiW6R1 (positive control); SS is a PCR product of pBinSiFAD2-GUS expression vector-containing Agrobacteria using the SiW6F1 and SiW6R1; SN is a PCR product of pBinSiFAD2-GUS expression vector-containing Agrobacteria using a pair of primers (forward primer: 5'-GAGGCTATTCGGCTATGACTG-3' and reverse primer: 5'-ATGGGAGCGGCGATACCGTA-3')) in npt II gene (kanamycin resistance marker gene), and V is a PCR product of pBI121 binary vector-containing Agrobacteria using the primers (forward primer: 5'-GAGGCTATTCGGCTATGACTG-3' and reverse primer: 5'-ATGGGAGCGGCGATACCGTA-3')) in the npt II gene. As a result, when the nptII primers were used, PCR products of about 700 bp long were obtained. On the other hand, when the gene-specific primers, the SiW6F1 and the SiW6R1 were used, PCR products of about 750 bp long were obtained. The result of FIG. 4C demonstrates that the pBinSiFAD2-GUS and pBI121 vectors were introduced into the Agrobacteria.

Figure 5:
FIG. 5 is a photograph of *Arabidopsis thaliana* transformed with *Agrobacteria* containing pBinSiFAD2-GUS or pBI121 vector.

After the Agrobacteria containing the pBinSiFAD2-GUS and pBI121 vectors were shaking-cultured at 28° C. for 2 days, the cultures were inoculated onto the pistils of Arabidopsis thaliana (ecotype Columbia) before flower opening by floral dip method [Clough and Bent, 1998, The Plant Journal]. FIG. 5 shows the Arabidopsis thaliana transformed with the Agrobacteria containing the pBinSiFAD2-GUS and pBI121 vectors of FIG. 4C. Here, a is the Arabidopsis thaliana transformed with the pBI121 vector-containing Agrobacteria and b is the Arabidopsis thaliana transformed with the pBinSiFAD2-GUS vector-containing Agrobacteria.

Figure 6:
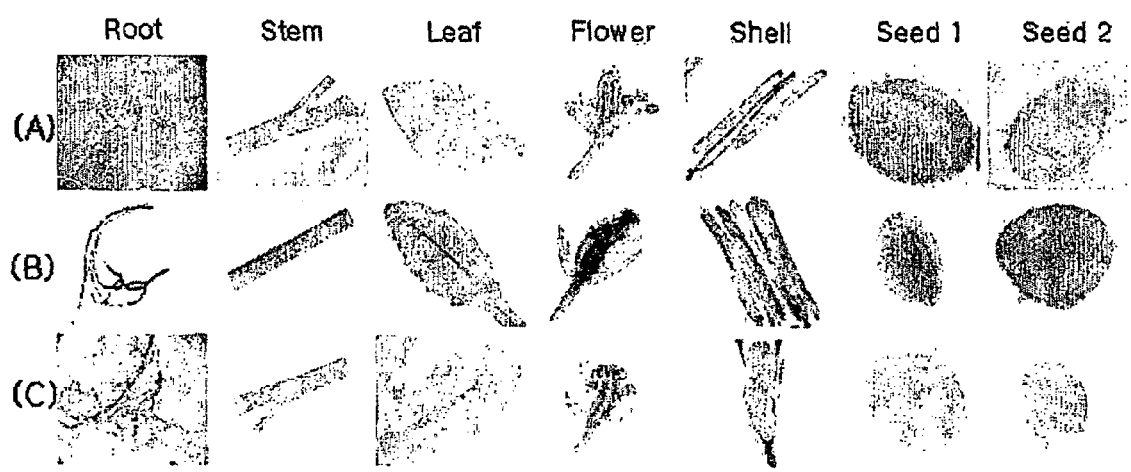
FIG. 6 is a histochemical staining result for GUS activity in various tissues of *Arabidopsis thaliana* transformed with *Agrobacteria* containing pBinSiFAD2-GUS vector.

Transgenic plants were selected on the MS media containing kanamycin (30 μg/ml). The GUS activity under the control of the Si-FAD2 promoter in various tissues of the transgenic plants was analyzed by a histochemical staining method and an enzymatic method. FIG. 6 is a histochemical staining result for GUS activity in various tissues of Arabidopsis thaliana transformed with the Agrobacteria containing the pBinSiFAD2-GUS vector under the control of the Si-FAD2 promoter. Here, (A) is Arabidopsis thaliana untreated, (B) is Arabidopsis thaliana transformed with pBI121 vector-containing Agrobacteria, and (C) is Arabidopsis thaliana transformed with pBinSiFAD2-GUS vector-containing Agrobacteria.

Figure 7A:
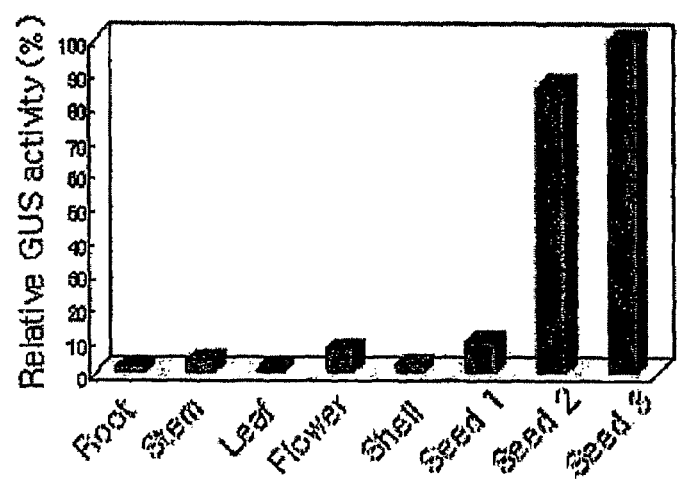
FIG. 7A is a graph showing relative GUS activity (%) in various tissues of *Arabidopsis thaliana* transformed with *Agrobacteria* containing pBinSiFAD2-GUS vector.
Figure 7B:
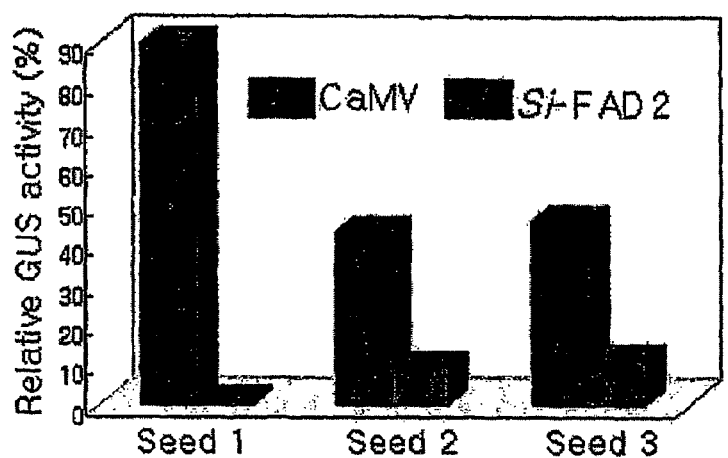
FIG. 7B is a graph showing relative GUS activity (%) in developing seeds of *Arabidopsis thaliana* transformed with *Agrobacteria* containing pBinSiFAD2-GUS or pBI121 vector.

FIG. 7A is a graph showing relative GUS activity (%) in various tissues of Arabidopsis thaliana transformed with Agrobacteria containing the GUS gene-containing binary vectors under the control of the Si-FAD2 promoter. Here, the minimal GUS activity was defined as 1%. Seed specimens were extracted depending on development stages (seeds 1: 5 to 7 days after flowering, seeds 2: 10 to 15 days after flowering, and seeds 3: 20 to 25 days after flowering). FIG. 7B is a graph showing relative GUS activity (%) in developing seeds of Arabidopsis thaliana transformed with Agrobacteria containing the pBinSiFAD2-GUS or pBI121 binary vector. Here, the minimal GUS activity was defined as 1%. As seen from FIGS. 6, 7A, and 7B, the GUS gene was expressed in an Arabidopsis thaliana seed-specific manner under the control of the Si-FAD2 promoter. In particular, the seeds that had developed for 10 to 25 days after flowering exhibited the highest level of GUS activity. These results demonstrate that the Si-FAD2 promoter can induce the expression of a foreign gene in a seed-specific manner, in particular a seed development stage-specific manner.

EXAMPLE 5

Analysis of Si-FAD2 Promoter Activity in Sesame Seeds

Figure 8A:
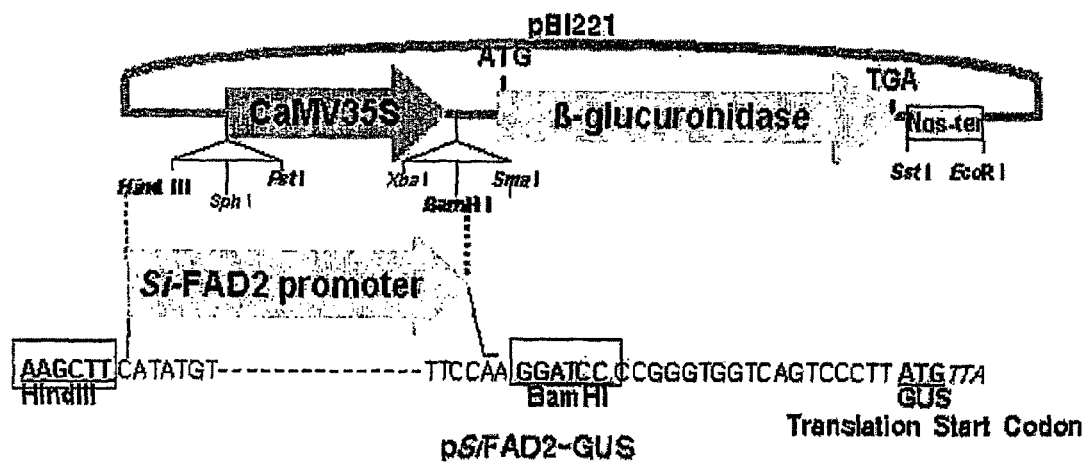
FIG. 8A is a diagram of a pSiFAD2-GUS expression vector constructed by inserting Si-FAD2 promoter into a pBI221 transient expression vector containing GUS gene.

In order to analyze the activity of the Si-FAD2 promoter in sesame seeds, a pSiFAD2-GUS transient expression vector containing the cloned Si-FAD2 promoter and the GUS reporter gene was constructed. First, the Si-FAD2 promoter region (−660 to +141) obtained in Example 4 was digested with HindIII and BamHI restriction enzymes. On the other hand, the CaMV35S promoter was removed from pBI221 (Cat. # 6019-1, Clontech, America) transient expression vector by using HindIII and BamHI restriction enzymes. The Si-FAD2 promoter was inserted into the CaMV35S promoter site of the pBI221 transient expression vector by using T4 DNA ligase. As a result, the pSiFAD2-GUS transient expression vector containing the Si-FAD2 promoter instead of the CaMV35S promoter was constructed. FIG. 8A shows a diagram of the pSiFAD2-GUS transient expression vector. Here, GUS is a reporter gene encoding β-Glucuronidase (which can be replaced with a foreign gene to be expressed). Nos-ter is the terminator for expression of nopaline synthase gene.

Figure 8B:
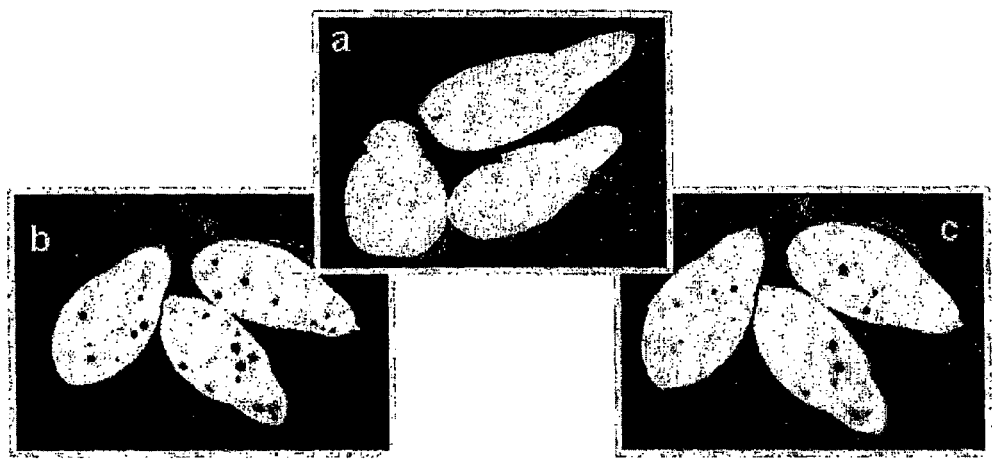
FIG. 8B is a histochemical staining result for GUS activity in developing seeds of sesame to which a pSiFAD2-GUS vector is introduced by particle bombardment.

Plasmid DNA from the pSiFAD2-GUS transient expression vector was purified using plasmid midi kit (Qiagen, America) and coated with 1.6 μm gold particles (Bio-rad, America). 2 ug of the plasmid DNA was mixed with 500 ug of the gold particles for one shot of particle bombardment (PDS1000/He gun, Bio-rad). The plasmid DNA mixed with the gold particles was bombarded under 1,100 psi (He gas) and incubated at 27° C. for 18 hours. The activity of the GUS, a foreign gene, under the control of the Si-FAD2 promoter, was analyzed by a histochemical staining method. FIG. 8B is a histochemical staining result for GUS activity in sesame developing seeds to which the pSiFAD2-GUS vector of FIG. 8A is introduced by particle bombardment. Here, a is the pBI221 vector containing no promoters, b is the pBI221 vector containing the CaMV35S promoter, and c is the pSiFAD2-GUS vector containing the Si-FAD2 promoter. As seen from FIG. 8B, the Si-FAD2 promoter can induce the expression of a foreign gene such as GUS in sesame developing seeds.

EXAMPLE 6

Construction of Binary Vectors Containing the Active Fragment of Si-FAD2 Promoter and Expression Enhancing Intron of Si-FAD2 Gene In this Example, the active fragment of the Si-FAD2 promoter involved in seed-specific expression was identified and the effect of the intron present on the Si-FAD2 gene on expression of a foreign gene in a transgenic plant was analyzed. For this, first, gene-specific primers containing HindIII (AAGCTT) and BamHI (GGATCC) restriction sites as presented in Table 1 were designed using the nucleotide sequence of the Si-FAD2 promoter.

kanamycin resistance marker gene encoding neomycin phosphotransferase II. Nos-pro and Nos-ter are respectively the promoter and terminator for plant expression of the NPTII. The GUS reporter gene is expressed in a plant under the control of the inserted promoter and the Nos terminator (Nos-ter).

Figure 9A:
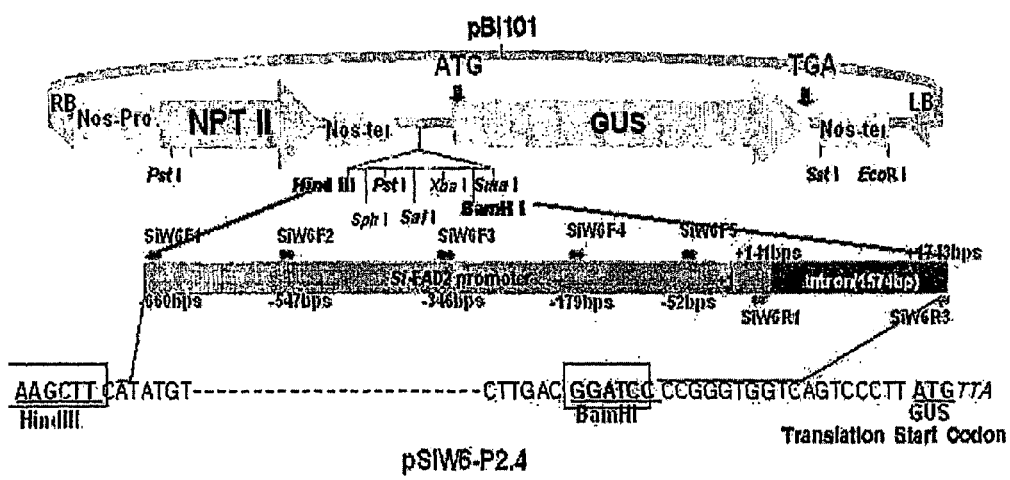
FIG. 9A is a diagram of a pSiW6-P2.4 expression vector constructed by inserting the promoter and intron of Si-FAD2 gene into a pBI101 binary vector containing GUS gene, and pSiW6-F1, pSiW6-F2, pSiW6-F3, pSiW6-F4, and pSiW6-F5 expression vectors constructed by inserting whole or part of the promoter of the Si-FAD2 gene into the pBI101 binary vector containing the GUS gene.
Figure 9B:
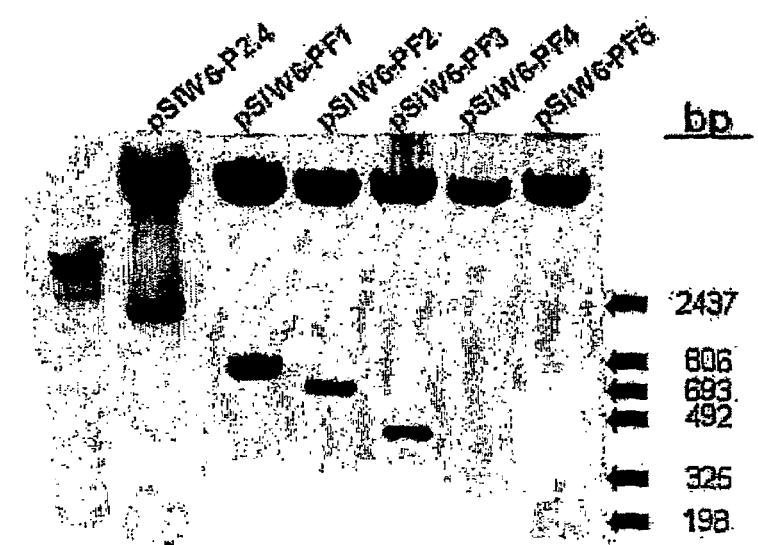
FIG. 9B is an electrophoretic photograph of the six expression vectors, pSiW6-P2.4, pSiW6-F1, pSiW6-F2, pSiW6-F3, pSiW6-F4, and pSiW6-F5 of FIG. 9A digested with HindIII and BamHI restriction enzymes.

The binary vectors thus constructed were introduced into *Escherichia. coli* and plasmid DNA was extracted by an alkaline lysis method [Sambrook et al., 2001]. The extracted plasmid DNA was digested with HindIII and BamHI followed by 0.7% agarose gel electrophoresis (FIG. 9B). FIG. 9B shows an electrophoretic result of the six binary vectors digested with HindIII and BamHI. Here, pSiW6-P2.4 is a binary vector containing the promoter and intron of a PCR product amplified with the gene-specific primers, SiW6F1 (−660 bp) and SiW6R3 (+1743 bp). pSiW6-F1 is a binary vector (identical to pBinSiFAD2-GUS binary vector) containing the promoter of a PCR product amplified with the gene-specific primers, SiW6F1 (−660 bp) and SiW6R1 (+141 bp). pSiW6-F2 is a binary vector containing the promoter of a PCR product amplified with the gene-specific primers, SiW6F2 (−547 bp) and SiW6R1 (+141 bp). pSiW6-F3 is a binary vector containing the promoter of a PCR product amplified with the gene-specific primers, SiW6F3 (−346 bp) and SiW6R1 (+141 bp). pSiW6-F4 is a binary vector containing the promoter of a PCR product amplified with the gene-specific primers, SiW6F4 (−179 bp) and SiW6R1 (+141 bp). pSiW6-F5 is a binary vector containing the promoter of a PCR product amplified with the gene-specific primers, SiW6F5 (−52 bp) and SiW6R1 (+141 bp).

EXAMPLE 7

Transformation of *Arabidopsis* with Binary Vectors

The six binary vectors (pSiW6-P2.4, pSiW6-F1, pSiW6-F2, pSiW6-F3, pSiW6-F4, and pSiW6-F5) constructed in

TABLE 1

| Primer type | Name | Nucleotide sequence | Tm |
|---|---|---|---|
| Forward | SiW6F1 | 5'-CCGAAGCTTCATATGTGAAATGTAATGGAAAATGCGAC-3' | 72° C. |
| primer | SiW6F2 | 5'-CCGAAGCTTGGGACATGCCACATTATGTGG-3' | 67° C. |
|  | SiW6F3 | 5'-CCGAAGCTTGTCCTAACCAGGTTTGAACAACC-3' | 67° C. |
|  | SiW6F4 | 5'-CCGAAGCTTGGAATGTGCACACTCCATGTG-3' | 67° C. |
|  | SiW6F5 | 5'-CCGAAGCTTGGGCCCCTCCTCAGACAGG-3' | 71° C. |
| Reverse | SiW6R1 | 5'-CTTGGATCCTTGGAAGGAGAAATCGCGTGAAAGCAC-3' | 75° C. |
| primer | SiW6R3 | 5'-CAAGGATCCGTCAAGCCGCCCCCAATTTAC-3' | 68° C. |

Next, PCR was performed by using sesame genomic DNA as a template with the above primers to obtain PCR products containing an original promoter region and a promoter region with partial deletion from the 5'-end. The PCR products thus obtained were digested with HindIII and BamHI and then inserted into the HindIII-BamHI restriction sites of pBI101 binary vectors (FIA. 4A, Cat. # 6017-1, Clontech, America) using T4 DNA ligase to construct binary vectors, pSiW6-P2.4, pSiW6-F1, pSiW6-F2, pSiW6-F3, pSiW6-F4, and pSiW6-F5 (FIG. 9A). FIG. 9A shows a diagram of the pSiW6-P2.4 binary vector containing the promoter and intron of the Si-FAD2 gene. Here, GUS is a reporter gene encoding β-glucuronidase (which can be replaced with a foreign gene to be expressed). NPTII is a Example 6 and the pBI121 binary vector (Cat.# 6018-1, Clontech, America) were introduced into *Agrobacterium tumefaciens* C58C1 [Suh et al., 2002, Molecules and Cells] by freeze-thaw method [An, G. 1987, Mothods in Enzymology]. According to the freeze-thaw method, the *Agrobacteria* were suspension-cultured in YEP media until O.D=0.5 followed by resuspending in 20 mM CaCl$_2$ solution. The suspension thus obtained was mixed with each of the seven binary vectors and incubated in liquid nitrogen for 1 minutes and then at 37° C. for 2 minutes. The transformed *Agrogacteria* were shaking-cultured at 28° C. for 2 days, and the cultures were inoculated onto the pistils of *Arabidopsis thaliana* (ecotype Columbia) before flower opening by floral dip method [Clough and Bent, 1998, The Plant Journal].

Figure 10:
FIG. 10 is a photograph of *Arabidopsis thaliana* transformed with *Agrobacteria* containing the six expression vectors, pSiW6-P2.4, pSiW6-F1, pSiW6-F2, pSiW6-F3, pSiW6-F4, and pSiW6-F5 of FIG. 9A and a pBI121 binary vector.

FIG. 10 is a photograph of *Arabidopsis thaliana* transformed with the *Agrobacteria* containing the six binary vectors of FIG. 9B and the pBI121 binary vector.

EXAMPLE 8

Histochemical Staining and Enzymatic Analysis for GUS Activity in Transformed *Arabidopsis Thaliana*

Seeds were harvested from the seven independent *Arabidopsis* transgenic lines constructed in Example 7 and spread on MS media containing kanamycin (30 µg/ml) to select kanamycin resistance transformants. GUS activity in the individual tissues of the selected transformants was analyzed by a histochemical staining method and an enzymatic method. In order to stain the individual tissues of the transformants, the individual tissues were immersed in a solution containing 1 mM X-glu (5-bromo-4-chloro-3-indolyl-β-glucuronide), 100 mM sodium phosphate (pH 7.0), 10 mM EDTA, 0.5 mM potassium ferricyanide, 0.5 mM potassium ferrocyanide, and 0.1% Triton X-100) and incubated at 37° C. for 12 hours. After removal of the solution, the stained tissues were rinsed with 100% ethanol until chlorophyll was exuded from the tissues. For the quantitative analysis of the GUS activity, the individual tissues were homogenized in a solution containing 50 mM sodium phosphate (pH 7.0), 10 mM EDTA, 0.1% Triton X-100, 0.1% sodium lauroylsarcosine, and 10 mM β-mercaptoethanol according to Jerrerson et al method [EMBO J. 6: 3901-3907, 1987] followed by centrifugation (12,000 g) to obtain supernatants. The supernatants were mixed with 1 mM MUG (4-methylumbelliferyl glucuronide) and incubated at 37° C. The reaction was terminated by adding 0.2 M $Na_2CO_3$. Fluorescence of the resultant reactions was measured at 365 and 455 nm by a fluorometer and plotted on the standard curve generated using the MUG standard to quantify the GUS activity.

Figure 11:
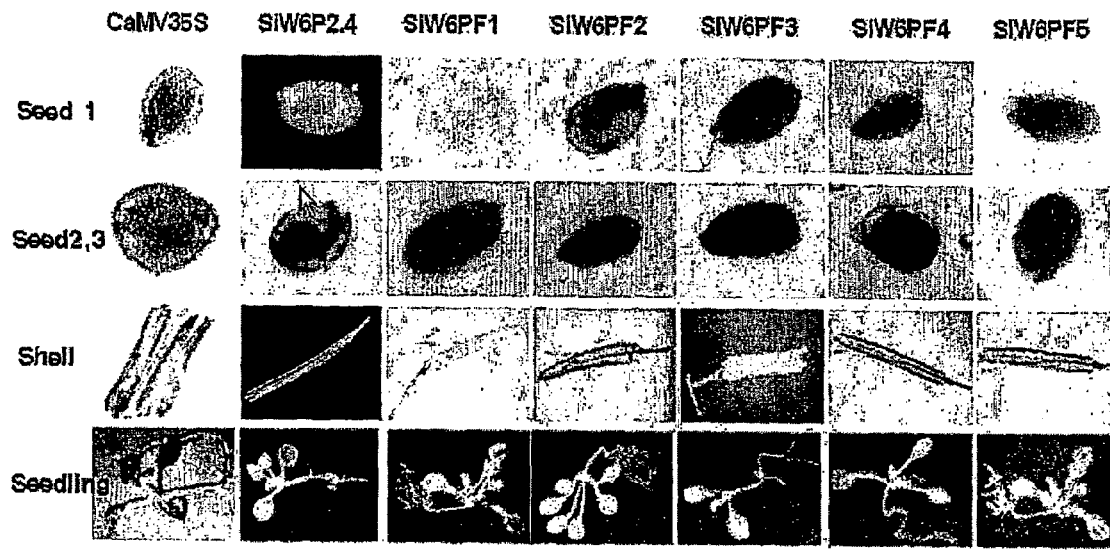
FIG. 11 is a histochemical staining result for GUS activity in developing seeds, shells covering the seeds, and seedlings germinated from the seeds of the seven types of the *Arabidopsis thaliana* of FIG. 10.

FIG. 11 is a histochemical staining result for GUS activity in developing seeds (seeds 1: 5 to 7 days after flower opening, seeds 2: 10 to 15 days after flower opening, seeds 3: 20 to 25 days after flower opening), shells covering the seeds, and seedlings germinated from the seeds of the *Arabidopsis thaliana* transformed with *Agrobacteria* containing the seven binary vectors. CaMV35S is *Arabidopsis thaliana* transformed with pBI121 binary vector. SiW6P2.4, SiW6F1, SiW6F2, SiW6F3, SiW6F4, and SiW6F5 are *Arabidopsis thaliana* transformed with pSiW6-P2.4, pSiW6-F1, pSiW6-F2, pSiW6-F3, pSiW6-F4, and pSiW6-F5, respectively. According to the results of FIG. 11, the Si-FAD2 promoter with a deletion of about 150-200 bp long from the 5'-end region also induced the expression of a foreign gene in a seed-specific manner. In addition, when the intron in the 5' UTR of the Si-FAD2 gene was inserted downstream of the Si-FAD2 promoter region (-660/+141) (SiW6P2.4, -660/+1743), GUS expression was detected in the shells and the cotyledons of the seedlings, in addition to the developing seeds.

Figure 12A:
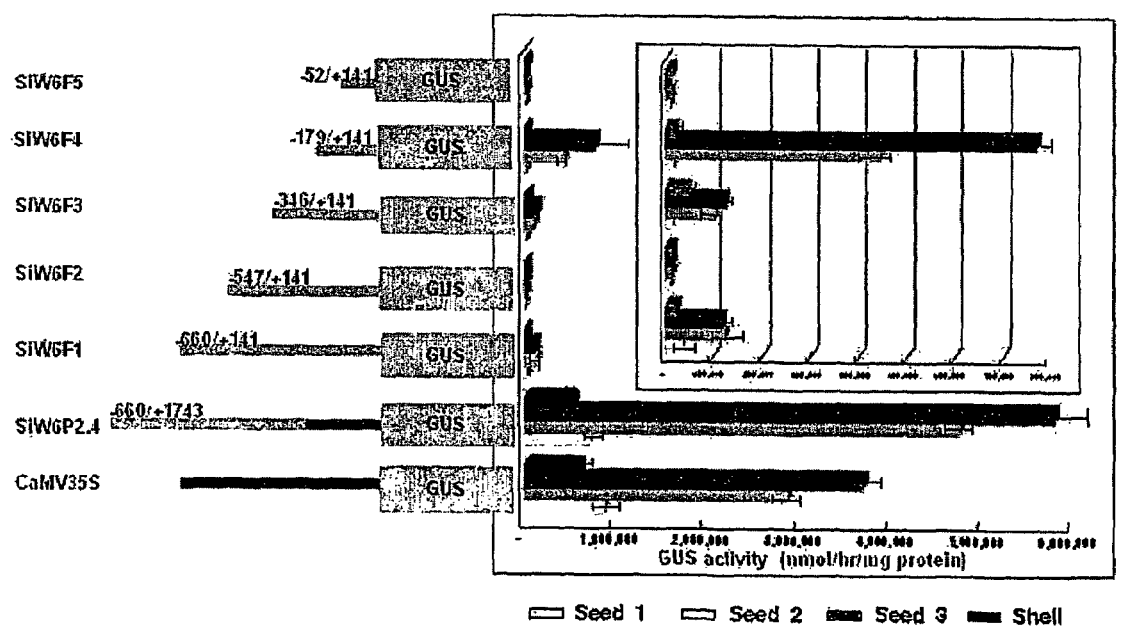
FIG. 12A is a graph showing quantitative GUS activity (nmol/hr/mg protein) in developing seeds and shells covering the seeds of the seven types of the *Arabidopsis thaliana* of FIG. 10.

FIG. 12A shows GUS activity in developing seeds (seeds 1: 5 to 7 days after flowering, seeds 2: 10 to 15 days after flowering, seeds 3: 20 to 25 days after flowering) and shells covering the seeds of the seven independent *Arabidopsis* transgenic lines obtained in FIG. 11. The GUS activity was analyzed in 10 transformants (T1 plant) per each of the seven transgenic plant constructs. As shown in FIG. 12A, the GUS activity of the transgenic plant constructs containing the Si-FAD2 promoter with a gradual deletion of 150-200 bp long from the 5'-end region was analyzed. As a result, SiW6F1 (-660/+141), SiW6F2 (-547/+141), SiW6F3 (-346/+141), and SiW6F4 (-179/+141) constructs exhibited the GUS activity of more than about 4 to 10-fold in the seeds 2, as compared to SiW6F5 construct (-52/+141). It can be seen from the result that the nucleotide sequence of -179 to -53 long in the Si-FAD2 promoter is an essential site that induces seed-specific expression. Also, SiW6P2.4 construct (-660/+1743) containing the intron exhibited the GUS activity of more than about 40-fold in the seeds 3 and more than 10-fold in the shells, as compared to the SiW6F1 construct (-660/+141) containing no intron. From the result, it can be seen that the Si-FAD2 promoter in the presence of the intron of the 5' UTR can greatly increase the expression level of a foreign gene in developing seeds and shells.

Figures 12B, 13:
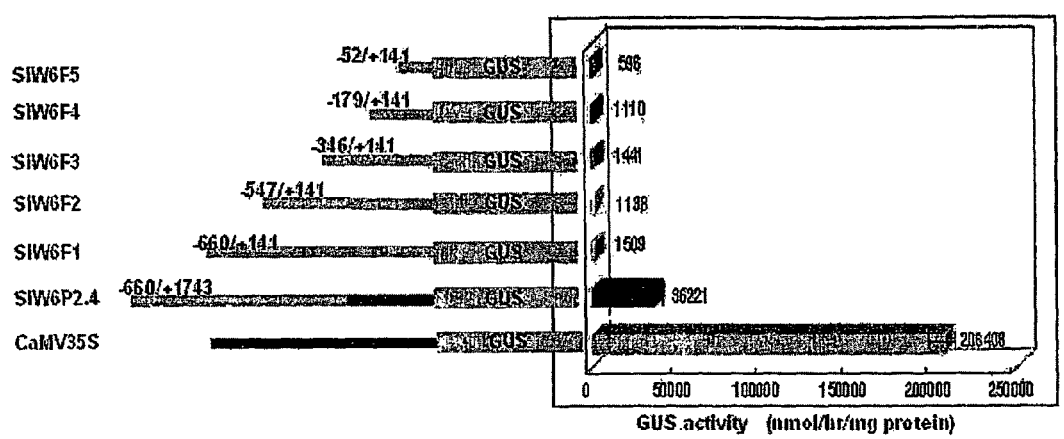
FIG. 12B is a graph showing quantitative GUS activity (nmol/hr/mg protein) in cotyledons of seedlings at 7 days after germination of the seeds of transformants selected after culturing the seeds of the seven types of the *Arabidopsis thaliana* of FIG. 10 in kanamycin (30 µg/ml)-containing media.
FIG. 13 is the nucleotide sequence (nucleotides −179 to −53 of SEQ ID NO: 3) of an active fragment of the seed-specific expression promoter of Si-FAD2 gene.

FIG. 12B shows GUS activity in seedlings (T2 plant) at 7 days after germination of the seeds of kanamycin (30 µg/ml) resistant transformants selected from the *Arabidopsis* transformants of FIG. 11. The GUS activity was analyzed in 5 transformants (T2 generation) per each of the seven transgenic plant constructs. GUS activity was not significantly observed in the seedlings of the SiW6F1, SiW6F2, SiW6F3, SiW6F4, and SiW6F5 constructs containing only the Si-FAD2 promoter. On the other hand, the SiW6P2.4 construct containing the promoter and intron of the Si-FAD2 gene exhibited about more than 30-fold increase of GUS activity in the cotyledons thereof, as compared to the SiW6F1 construct containing no intron. From these results, it can be seen that while the Si-FAD2 promoter induces the expression of a foreign gene in a developing seed, the intron of the Si-FAD2 gene can enhance the expression of a foreign gene in a seed-, shell-, and seedling cotyledon.

INDUSTRIAL APPLICABILITY

As is apparent from the above descriptions, the present invention provides the nucleotide sequence of sesame microsomal oleic acid desaturase (Si-FAD2) gene and the Si-FAD2 promoter. The Si-FAD2 promoter induces the expression of a foreign gene in a plant in a seed development stage-specific manner. The present invention also provides a method for expressing a foreign gene in a transgenic plant using the Si-FAD2 promoter. Therefore, the present invention is useful in producing a useful product in a seed-specific manner or functionally modifying a common product in a seed. Also, according to the present invention, the promoter can be used together with the intron for expression enhancement, thereby increasing the expression level of an inserted gene in a seed by at least 40-fold. Therefore, the present invention can be used in development of a transgenic plant which induces large-scale expression of a foreign gene in a seed-specific manner.

What is claimed is:

1. An isolated seed-specific promoter comprising SEQ ID NO: 3 or an active fragment thereof.

2. The seed-specific expression promoter of claim 1, which comprises the nucleotide sequence as set forth in SEQ ID NO: 3.

3. A seed-specific expression vector comprising the promoter of claim 1.

4. The seed-specific expression vector of claim 3, which is constructed by inserting the promoter upstream of a foreign gene of a binary vector.

5. The seed-specific expression vector of claim 4, wherein said foreign gene encodes a FAD2.

6. The seed-specific expression vector of claim 3, which is constructed by inserting the promoter upstream of a foreign gene of a transient expression vector.

7. The seed-specific expression vector of claim 6, wherein said foreign gene encodes a FAD2.

8. A transgenic plant transformed with the seed-specific expression vector of claim 3.

9. A method for expressing a foreign gene in a transgenic plant transformed with the seed-specific expression vector of claim 3.

10. The seed-specific expression vector of claim 3, which further comprises an intron for enhancement of gene expression comprising nucleotides 149 to 1722 of SEQ ID NO. 1.

* * * * *

SEQUENCE LISTING

<160> NUMBER OF SEQ ID NOS: 3

<210> SEQ ID NO 1
<211> LENGTH: 3102
<212> TYPE: DNA

```
<213> ORGANISM: Sesamum indicum
<220> FEATURE:
<221> NAME/KEY: 5'UTR
<222> LOCATION: (1)..(1746)
<220> FEATURE:
<221> NAME/KEY: intron
<222> LOCATION: (149)..(1722)
<220> FEATURE:
<221> NAME/KEY: 3'UTR
<222> LOCATION: (2899)..(3102)

<400> SEQUENCE: 1
```

| | | | | | |
|---|---|---|---|---|---|
| aacgccactc | aaatatttca | ccaccaccac | caccagaaca | ttcagaaaca | agaaataaac | 60 |
| acacacacac | tataaaacag | ttcttgcgaa | agaaggaaag | cgcttccgca | gaagtgcttt | 120 |
| cacgcgattc | ctccttccaa | gttttcaggt | aacgtgcccc | cttttctctt | ctcttctatt | 180 |
| ctctttctc | ataattcatg | atcaatcttt | gagtattttg | gtgtttgtgt | gtctcaagaa | 240 |
| aaccgcattt | ttattttctt | gcaatggtgt | ctttatttcc | tgtcgttttt | ttcagctatt | 300 |
| aatgttcttt | tgatgtagat | gaggtttaat | cgtatgttct | tgagctgcat | tacctgatga | 360 |
| ttcatggatc | tgaggaatgt | atgcgatttt | ttattttgt | tttatttttt | ggtgggcttt | 420 |
| cccaagaaga | atctatttgg | ggttattctt | gtgtggtttg | gtgcaaatct | ttggatttta | 480 |
| cgcagtattg | gtgtctggac | cacatgattg | tgtcatttat | atttggattt | tgtctttatc | 540 |
| tttgtatgca | tgtgggatgc | aggaagaaaa | aactgtggta | aatgtctttg | aagagattga | 600 |
| tttagcatat | atacaaggtt | gcctgggctt | cagttttgat | gattttgatg | tacattgtgg | 660 |
| agatttgatg | ggttgcatgt | ggctcaaatc | ttcttgtaag | atttgttttt | tgtccaaaaa | 720 |
| atttgggatt | tttccacttt | tattgaacag | tagatctttt | cctgtttcaa | cccaaaagtt | 780 |
| atttcggttt | gaagttttac | atcatagata | taattagtaa | taaatttcgg | ttaggtccgt | 840 |
| aaagaatcat | taattacatc | aattaatatt | gtttaatgta | caaaaagagg | gaatttatgg | 900 |
| tgatatctat | gaagccatgc | tatgcctggc | tggaattccg | tcgatgaaaa | agacagattc | 960 |
| cggtgtgtgg | tagatttcac | tgttagtgaa | taccccactt | caaagaacgg | tgctgattca | 1020 |
| actgctctag | tcctcaggat | tttagtacta | cttgtttgct | gtttggaaca | catggctgaa | 1080 |
| aataaatgtc | tgcttttcga | ccttggcgct | tagagaattt | actaccacat | ctcattttta | 1140 |
| gcatcccaac | gatgatttct | gctgtcagaa | tgaatgaatt | gactaagagc | aactcggtta | 1200 |
| tttgagattg | aattggttgt | ttgtgattgt | tgttgatttg | ttttgtcgt | tatgatcttt | 1260 |
| tgaggtattc | gccatacaat | gctgatacta | gtcgttgtga | ttttccggta | tatgtatttg | 1320 |
| tgacgtatcg | ttctgtagtt | tggtaactaa | tagaatgcat | gtggtggtaa | ctaatagaat | 1380 |
| gcatgttgta | gtaacaaatg | cacattgtag | attctcgtgg | attttcgggg | tgttcgttac | 1440 |
| cagcacattg | ccgattctgg | tatgattttt | gtcgtgttca | ttgtttagtt | gcctttcttg | 1500 |
| gctgccacta | tttcattgag | aatgtaggac | gttgttcgat | gcaaagaac | ttttgccgac | 1560 |
| tagaatgcag | gtggcaatct | ggaatctcct | attatgggag | gaactactgt | aattgggagg | 1620 |
| ttttgattca | gacaatctag | taacagtcta | gaagctactt | tgcctttaaa | tctcaatgac | 1680 |
| cttaaacgcc | atgatggaga | catttgaatc | catgttttgc | aggtaaattg | ggggcggctt | 1740 |
| gacaaaatgg | gagccggagg | acgcatgtct | gatccaacaa | cgaaagacga | acaaaagaag | 1800 |
| aacccctcc | aacgggtgcc | ttacgcaaag | cctccattca | cactcggtga | catcaagaag | 1860 |
| gccattccac | cacactgctt | cgagagatcc | gtcagccgtt | cgttctccta | tgtcgtttac | 1920 |
| gatctcgtca | ttgttttcct | tctctactac | attgcgactt | cttacttcca | tctgctgcca | 1980 |

```
tccccatact gctacctagc ttggcccatt tactgggctg tacaaggctg cgtttgcacc      2040
ggaatctggg tcattgccca tgaatgtggc caccatgcat tcagcgatta ccagtggctt      2100
gacgacacag ttggcctcat cctgcactct gccctgctcg tgccctattt ctcatggaaa      2160
tacagccacc gccgccacca ctccaacact ggatcccttg agcgtgacga agtcttcgtc      2220
ccaaagccaa aatccagagt ctcgtggtac tccaaatact tgaacaatcc acttggcaga      2280
gtcatcacac ttgtggttac tcttactctc ggttggcctc tatacttgct gtttaatgtc      2340
tctggcaggc cttacaaccg ttttgcatgc cactttgacc catatggtcc aatatataat      2400
gaccgtgaga gacttcaaat cttcatctcc gatgctggta taattgctgc tgtatgtgtg      2460
ctttatcgtg ttgctttggt caaagggttg gcttggctgg tatgtgttta tggggtaccg      2520
ttactcattg tcaacggttt ccttgttttg atcacattcc ttcagcacac tcacccttcg      2580
ttgccgcact atgattcttc cgagtgggac tggctaaggg gagctcttgc aactgtcgac      2640
agagattatg gggtgctaaa taaggtgttc cataacatca cagatacgca cgtgactcac      2700
caccttttct caacgatgcc acattaccat gcaatggagg caactaaggc aatcaagccc      2760
atactgggcc agtattatca gtttgatgga accccgtttt acaaggcgat gtggagggag      2820
gcaaaggaat gtctgtatgt cgagccagac gagagtactc cagacaaggg tgtattctgg      2880
tacaagaaca agttctgaag ccgaataaca tgtggttagt gaaaatggcg tcttcttatt      2940
ttgtcctatg gagatggagg aacatcatca tgtttctttt tcttcttat aagatgcgtc       3000 ctttgttagt gtattctctg catgtaataa aataaacttc tacccgaaac cttgtctgtg      3060
ctggtcggat tctagttctg caataaattg tcaagtttag tg                         3102
```

<210> SEQ ID NO 2
<211> LENGTH: 383
<212> TYPE: PRT
<213> ORGANISM: Sesamum indicum

<400> SEQUENCE: 2

```
Met Gly Ala Gly Gly Arg Met Ser Asp Pro Thr Thr Lys Asp Glu Gln
  1               5                  10                  15

Lys Lys Asn Pro Leu Gln Arg Val Pro Tyr Ala Lys Pro Pro Phe Thr
             20                  25                  30

Leu Gly Asp Ile Lys Lys Ala Ile Pro Pro His Cys Phe Glu Arg Ser
         35                  40                  45

Val Ser Arg Ser Phe Ser Tyr Val Val Tyr Asp Leu Val Ile Val Phe
     50                  55                  60

Leu Leu Tyr Tyr Ile Ala Thr Ser Tyr Phe His Leu Leu Pro Ser Pro
 65                  70                  75                  80

Tyr Cys Tyr Leu Ala Trp Pro Ile Tyr Trp Ala Val Gln Gly Cys Val
                 85                  90                  95

Cys Thr Gly Ile Trp Val Ile Ala His Glu Cys Gly His His Ala Phe
            100                 105                 110

Ser Asp Tyr Gln Trp Leu Asp Asp Thr Val Gly Leu Ile Leu His Ser
        115                 120                 125

Ala Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Pro Lys Ser Arg Val Ser Trp Tyr Ser Lys Tyr Leu Asn Asn Pro Leu
                165                 170                 175
```

```
Gly Arg Val Ile Thr Leu Val Val Thr Leu Thr Leu Gly Trp Pro Leu
                180                 185                 190
Tyr Leu Leu Phe Asn Val Ser Gly Arg Pro Tyr Asn Arg Phe Ala Cys
            195                 200                 205
His Phe Asp Pro Tyr Gly Pro Ile Tyr Asn Asp Arg Glu Arg Leu Gln
        210                 215                 220
Ile Phe Ile Ser Asp Ala Gly Ile Ile Ala Ala Val Cys Val Leu Tyr
225                 230                 235                 240
Arg Val Ala Leu Val Lys Gly Leu Ala Trp Leu Val Cys Val Tyr Gly
                245                 250                 255
Val Pro Leu Leu Ile Val Asn Gly Phe Leu Val Leu Ile Thr Phe Leu
                260                 265                 270
Gln His Thr His Pro Ser Leu Pro His Tyr Asp Ser Ser Glu Trp Asp
                275                 280                 285
Trp Leu Arg Gly Ala Leu Ala Thr Val Asp Arg Asp Tyr Gly Val Leu
            290                 295                 300
Asn Lys Val Phe His Asn Ile Thr Asp Thr His Val Thr His His Leu
305                 310                 315                 320
Phe Ser Thr Met Pro His Tyr His Ala Met Glu Ala Thr Lys Ala Ile
                325                 330                 335
Lys Pro Ile Leu Gly Gln Tyr Tyr Gln Phe Asp Gly Thr Pro Phe Tyr
            340                 345                 350
Lys Ala Met Trp Arg Glu Ala Lys Glu Cys Leu Tyr Val Glu Pro Asp
                355                 360                 365
Glu Ser Thr Pro Asp Lys Gly Val Phe Trp Tyr Lys Asn Lys Phe
            370                 375                 380

<210> SEQ ID NO 3
<211> LENGTH: 660
<212> TYPE: DNA
<213> ORGANISM: Sesamum indicum
<220> FEATURE:
<221> NAME/KEY: promoter
<222> LOCATION: (1)..(660)
<223> OTHER INFORMATION: promoter of microsomal oleic acid desaturase
      coding gene

<400> SEQUENCE: 3
catatgtgaa atgtaatgga aaatgcgaca agaattgcaa tagagaaaat ccaatttgca      60
gagattacat gaaagaatt tgtacaaata gcatatatat gttaaaatga atgggacat      120 gccacattat gtggaataaa aaagacaatt tgcttggaat taattataga ataaatgtgt     180
tacatttaat atgtgattaa tcactttttt tgaattgtac atctatcaca tgacaagttc     240
attatatttg acatataatt tgtttatgtc tagtcaagcc taattaaatt tctcggaaag     300
cacaaaattt ttttgtccta accaggtttg aacaaccaaa caaatcacaa agcaggtgta     360
tcgcacttgc gatgtgatcg gtcactttt ctaaattgta catcattcac acgacaactg     420
tattgtgctc caagttcaat tgagtgcggt tggagctata atttccttga acacacaatg     480
tggaatgtgc acactccatg tgggccaatg agcggatgac acgtggcggg caacttacct     540
cgttacgttg aggcatgcat gaaaggggga tctcttgagg tggagggtg gggcgggg       600 ttggggggg gcccctcctc agacaggtct atatttatga gacctcgtaa ggcagaacgc     660
```